US010874310B2

(12) United States Patent
McDuff et al.

(10) Patent No.: US 10,874,310 B2
(45) Date of Patent: Dec. 29, 2020

(54) METHODS AND APPARATUS FOR PHYSIOLOGICAL MEASUREMENT USING COLOR BAND PHOTOPLETHYSMOGRAPHIC SENSOR

(71) Applicant: Massachusetts Institute of Technology, Cambridge, MA (US)

(72) Inventors: Daniel McDuff, Seattle, WA (US); Rosalind Picard, Newton, MA (US); Sarah Pratt, Lafayette, CO (US)

(73) Assignee: Massachusetts Institute of Technology, Cambridge, MA (US)

( * ) Notice: Subject to any disclaimer, the term of this patent is extended or adjusted under 35 U.S.C. 154(b) by 407 days.

(21) Appl. No.: 15/994,968

(22) Filed: May 31, 2018

(65) Prior Publication Data

US 2018/0279893 A1 Oct. 4, 2018

Related U.S. Application Data

(63) Continuation of application No. 14/677,869, filed on Apr. 2, 2015, now Pat. No. 10,028,669.

(60) Provisional application No. 61/973,842, filed on Apr. 2, 2014.

(51) Int. Cl.
*A61B 5/00* (2006.01)
*A61B 5/024* (2006.01)

(52) U.S. Cl.
CPC ........ *A61B 5/02427* (2013.01); *A61B 5/0022* (2013.01); *A61B 5/0077* (2013.01); *A61B 5/02405* (2013.01); *A61B 5/7203* (2013.01); *A61B 5/7239* (2013.01); *A61B 2576/00* (2013.01)

(58) Field of Classification Search
CPC .............. A61B 2576/00; A61B 5/0205; A61B 5/02405; G06K 9/00255; G06K 9/624
See application file for complete search history.

(56) References Cited

U.S. PATENT DOCUMENTS

| | | | |
|---|---|---|---|
| 6,771,314 | B1 | 8/2004 | Bawolek et al. |
| 2011/0251493 | A1 | 10/2011 | Poh et al. |
| 2012/0195473 | A1 | 8/2012 | De Haan et al. |

OTHER PUBLICATIONS

Poh, M., et al., 2010, Non-contact, automated cardiac pulse measurements using video imaging and blind source separation. Optics Express, vol. 18, Issue 10, 2010, pp. 10762-10774.

(Continued)

*Primary Examiner* — Mark D Remaly
(74) *Attorney, Agent, or Firm* — Stephen R. Otis

(57) ABSTRACT

In illustrative implementations of this invention, a photoplethysmographic device measures variations of light that is reflected from, or transmitted through, human skin. In some implementations, the device includes a camera that takes the measurements remotely. In others, the device touches the skin during the measurements. The device includes a camera or other light sensor, which includes at least orange, green and cyan color channels. In some cases, such as a contact device, the device includes three or more colors of active light sources, including at least orange, green and cyan light sources. A computer analyzes the sensor data, in order to estimate a cardiac blood volume pulse wave. For each cardiac pulse, a computer detects the systolic peak and diastolic inflection of the wave, by calculating a second derivative of the wave. From the estimated wave, a computer estimates heart rate, heart rate variability and respiration rate.

7 Claims, 8 Drawing Sheets

(56) References Cited

OTHER PUBLICATIONS

Schmitt, J., et al., 1986, New methods for whole blood oximetry. Annals of Biomedical Engineering 1986, vol. 14, Issue 1, pp. 35-52.
Takawaza, K., et al., 1998, Assessment of Vasoactive Agents and Vascular Aging by the Second Derivative of Photoplethysmogram Waveform. Hypertension, Aug. 1998, vol. 32, No. 2, pp. 365-370.
Verkruysse, W., et al., 2008, Remote plethysmographic imaging using ambient light. Optics Express, Dec. 2008, vol. 16, No. 26, pp. 21434-21445.
Poh, M., et al., 2011, Advancements in Noncontact, Multiparameter Physiological Measurements Using a Webcam. IEEE Transactions on Biomedical Engineering, vol. 58, Issue 1, 2011, pp. 7-11.

METHODS AND APPARATUS FOR PHYSIOLOGICAL MEASUREMENT USING COLOR BAND PHOTOPLETHYSMOGRAPHIC SENSOR

RELATED APPLICATIONS

This application is a continuation of U.S. application Ser. No. 14/677,869 filed Apr. 2, 2015, which claims the benefit of U.S. Provisional Patent Application No. 61/973,842 filed Apr. 2, 2014.

FIELD OF TECHNOLOGY

The present invention relates generally to photoplethysmography.

COMPUTER PROGRAM LISTING

Attached is an ASCII text file multi_band_code.txt, created Mar. 25, 2014, with a size of about 22 KB (the "Source Code"). This ASCII text file comprise a computer program listing for software in a prototype implementation of this invention. This ASCII text file is incorporated by reference herein.

SUMMARY

In exemplary implementations of this invention, a photoplethysmographic (PPG) sensor measures variations of intensity of light. The light is reflected from, or transmitted through, skin of a human. The intensity of the light varies due to a cardiac blood volume pulse (BVP) wave. The BVP wave occurs when a pulse of blood due to a heartbeat passes through blood vessels at or near the skin (including the dermis and subcutaneous tissue). Thus, the BVP wave is a peripheral pulse wave that occurs at or near the skin.

A computer analyzes the PPG sensor data, in order to estimate a BVP wave. From the estimated BVP wave, a computer estimates inter-beat intervals (IBIs), which are the same as the time intervals between successive systolic peaks of the BVP wave. From the estimated BVP wave, a computer also estimates the time intervals between the systolic peak and diastolic inflection of the BVP wave.

The interval between the systolic peak and diastolic inflection of the BVP wave is difficult to measure, because the diastolic inflection is hard to detect. If the diastolic inflection is a peak in the BVP wave, it is typically much smaller than the systolic peak, and in some cases, the diastolic inflection is not a peak at all.

In illustrative implementations of this invention, this problem is mitigated by computing the second derivative of the estimated BVP wave, and then inverting the estimated BVP wave. For each cardiac pulse, a computer: (a) detects the highest peak of the inverted second derivative of the BVP wave and identifies that highest peak as the systolic peak; and (b) detects the second highest peak of the inverted second derivative of the BVP wave, and identifies that second highest peak as the diastolic inflection. Alternatively, the computer detects the next peak in time (after the diastolic peak) of the inverted second derivative of the BVP wave, and identifies that next peak in time as the diastolic inflection. For each cardiac pulse: (a) the highest peak of the inverted second derivative of the BVP wave occurs at the systolic peak of the BVP wave; (b) the second highest peak of the inverted second derivative of the BVP wave (which is also the next peak in time after the highest peak of the inverted second derivative) occurs at the diastolic inflection of the BVP wave. Thus, for each cardiac pulse, the diastolic inflection of the BVP wave occurs at a peak of the inverted second derivative that is next in magnitude, and next in time, after the highest peak of the inverted second derivative.

Alternatively, in some cases, a computer detects troughs in a non-inverted second derivative (instead of peaks in an inverted second derivative) of the BVP wave, in order to identify the systolic peak and diastolic inflection of the BVP wave. In that case, for each cardiac pulse, a computer identifies the systolic peak of the BVP wave as the deepest trough of the non-inverted second derivative of the BVP wave and the diastolic inflection of the BVP wave as the second deepest trough (and next trough in time after the diastolic trough) of the non-inverted second derivative.

From the estimated BVP wave, a computer estimates physiological parameters of the human, including one or more of the following parameters: heart rate (HR), heart rate variability (HRV), the low-frequency component of the HRV power spectra (LF-HRV), the high-frequency component of the HRV power spectra (HF-HRV), and the low-frequency/high frequency ratio of the HRV power spectra. In addition, in some cases, a computer estimates breathing rate (BR) of the human from the PPG data.

In some implementations of this invention, the PPG sensor comprises a digital video camera, and the PPG data is gathered remotely. The camera captures video images of the human's skin. For example, in some cases, the camera captures video images of the human's face, while the camera is positioned at a distance of 3 meters from the human's face. Alternatively, the camera images other regions of the human's skin. Alternatively, the camera is positioned at distances other than 3 meters from the human's face.

In some implementations, the sensor of the digital video camera includes three or more color channels. The three or more color channels include orange (O), green (G) and cyan (C) color channels. In some cases, the sensor of the camera includes other color channels, in addition to the OGC color channels. For example, in some cases, the video camera comprises a 5 band digital video camera with ROGCB color channels (i.e., red, orange, green, cyan and blue color channels).

In a prototype of this invention, a video camera takes video images of a human face while remote from the face, e.g., more than a meter from the face. In the prototype, the video camera has a CMOS sensor with five color channels: red, orange, green, cyan and blue.

Experiments have been performed to test the accuracy of the prototype. The experiments show that a combination of orange, green and cyan color channels performs better than other combinations of the five color channels. Specifically, in the experiments, correlations are determined. The correlations are between measurements taken by the prototype and measurements taken by a conventional (prior art) FDA-approved, contact PPG device. The correlations are higher when the prototype uses the OGC (orange, green, cyan) combination of color channels than when the prototype uses any other combination of the color channels.

In some implementations of this invention, the PPG data is gathered while the housing of a PPG sensor is in contact with the human's skin. The contact PPG sensor includes a light source module and a light sensor module. The light source module includes different colors of light sources, and the light sensor module includes different color channels. In some cases, for each color of light source, the light sensor includes a color channel of the same color. For example, in some implementations, the contact PPG sensor has a light source module that includes at least orange, green and cyan light sources and has a light sensor module that includes at least orange, green and cyan color channels.

In illustrative implementations of this invention, the PPG sensor (including a remote or contact sensor) has many practical applications. Here are some non-limiting examples:

In some cases, measurements taken by the PPG sensor are analyzed to detect arterial stiffness, which is an early sign of atherosclerosis (hardening of the arteries). Properties of the BVP waveform are indicative of small and medium arterial stiffness due to the relationship between arterial elasticity and the reflection of the PPG signal.

In some cases, heart rate and heart rate variability measurements taken by a remote or contact PPG device are used in infant monitoring, detection of cardiac diseases and stress monitoring.

The description of the present invention in the Summary and Abstract sections hereof is just a summary. It is intended only to give a general introduction to some illustrative implementations of this invention. It does not describe all of the details and variations of this invention. Likewise, the descriptions of this invention in the Field of Technology section is not limiting; instead it identifies, in a general, non-exclusive manner, a field of technology to which exemplary implementations of this invention generally relate. Likewise, the Title of this document does not limit the invention in any way; instead the Title is merely a general, non-exclusive way of referring to this invention. This invention may be implemented in many other ways.

The above Figures show some illustrative implementations of this invention, or provide information that relates to those implementations. However, this invention may be implemented in many other ways.

DETAILED DESCRIPTION

In exemplary implementations of this invention, a photoplethysmograph sensor measures variations of intensity of light. The light is reflected from, or transmitted through, skin of a human.

A computer analyzes PPG data gathered by the photoplethysmograph, in order to estimate a cardiac blood volume pulse (BVP) wave. The BVP wave that is measured is a peripheral pulse wave that occurs at or near the skin.

Figure 1:
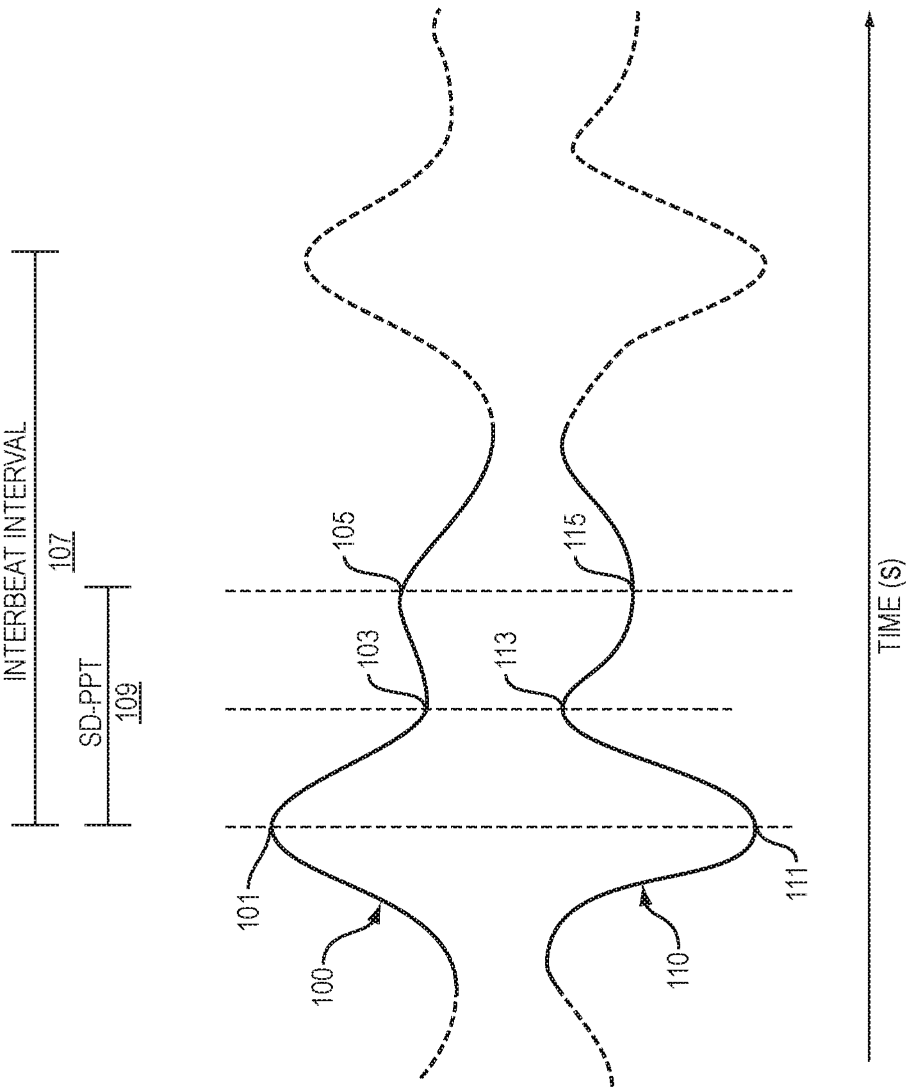
FIG. 1 shows a blood volume pulse (BVP) wave and the second derivative of the BVP wave.

FIG. 1 shows a cardiovascular blood volume pulse (BVP) wave 100 that occurs at or near facial skin of a human. For each heartbeat, the BVP wave 100 exhibits a systolic peak 101, a dicrotic notch 103, and a diastolic inflection 105. The diastolic inflection 105 may be, but is not always, a peak. In the example shown in FIG. 1, the diastolic inflection 105 is a peak. However, in many persons under many circumstances, the diastolic inflection 105 is an inflection point on the BVP curve, but is not a peak of the BVP curve.

In illustrative implementations of this invention, a computer computes a second derivative of the BVP wave, in order to more accurately determine diastolic inflections. FIG. 1 shows a second derivative 110 of the BVP wave 100. The second derivative 110 has a systolic dip 111, a dicrotic peak 113 and a diastolic dip 115.

The inter-beat interval (IBI) 107 is the interval between successive systolic peaks. The so-called systolic-diastolic peak-to-peak time (SD-PPT) 109 is the interval between the systolic peak 101 and diastolic inflection 105 ("so-called", because the diastolic "peak" is, in many cases, not a peak but merely an inflection).

In some implementations of this invention, a camera that is remote from the skin is used for photoplethysmographic (PPG) measurements of the BVP wave in the skin. In these non-contact implementations, the camera is not touching the skin, and is not housed in apparatus that touches the skin. For example, in some cases, the camera is positioned 3 meters from the skin.

Figure 2A:
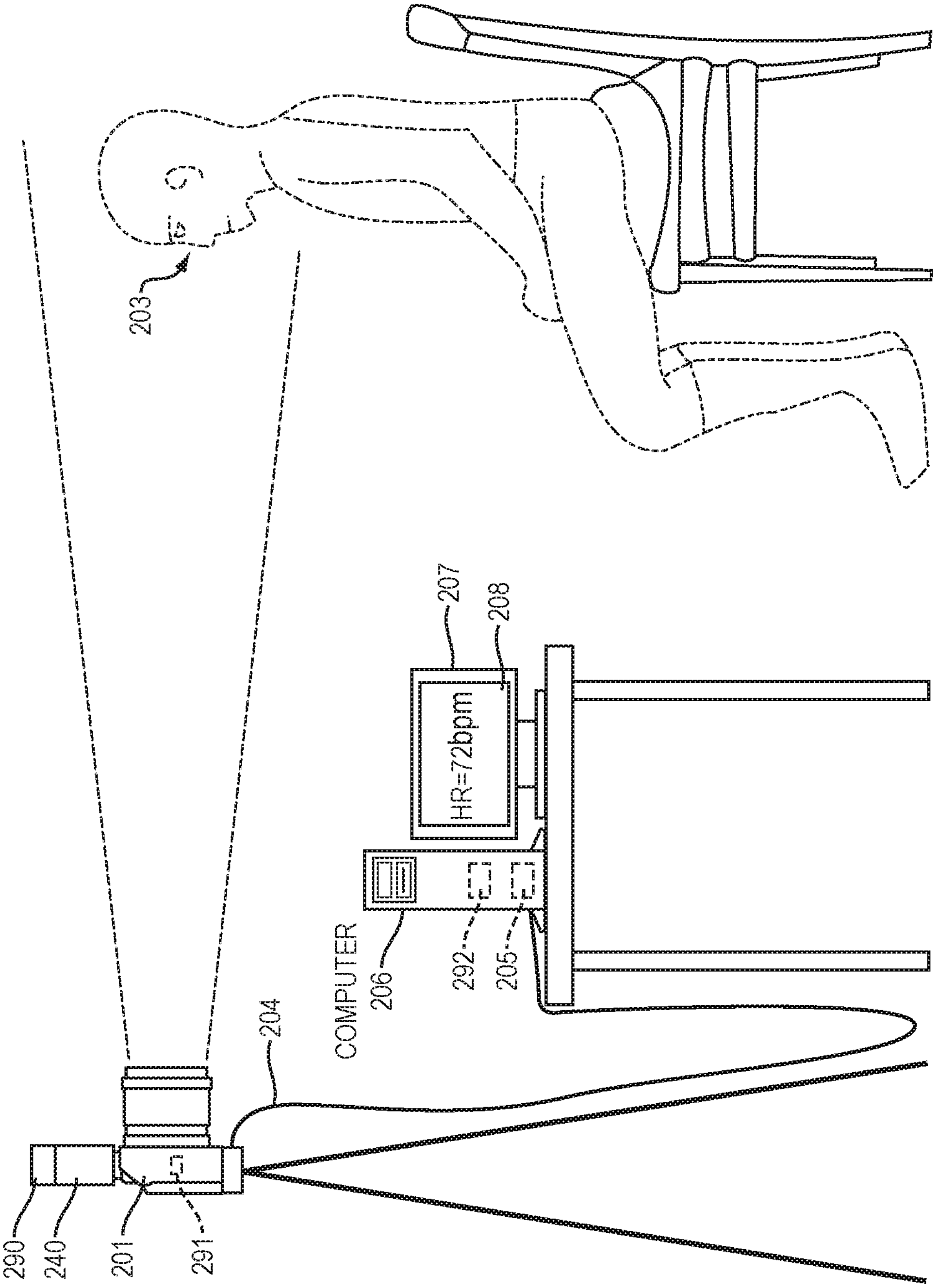
FIG. 2A shows hardware for non-contact (remote) PPG measurements using a color band video camera.

FIG. 2A shows hardware for non-contact (remote) PPG measurements using a color band video camera, in an illustrative implementation of this invention. In FIG. 2A, a camera 201 images the face 203 of a human. In many implementations, the face is only passively illuminated, that is, illuminated only by ambient light.

The camera 201 has at least three color bands, including orange, green and cyan color bands. In some cases, the camera 201 has more than three color bands. For example, in some cases, the camera 201 has five color bands (red, orange, green, cyan and blue).

The camera 201 exports visual data (e.g., a video stream) to a computer 206. The computer 206 takes the visual data as input, calculates IBIs and SD-PPTs, and determines physiological parameters of the human, including one or more of the following parameters: heart rate, breath rate, heart rate variability (HRV), a high-frequency component of the HRV, and a low-frequency component of the HRV. The computer 206 stores data in memory 205. The computer 206 also controls an I/O device 207, such as computer monitor or other display screen. The computer 206 causes the I/O 207 to display a graphical user interface (GUI) 208. The GUI 208 displays, in human readable format, physiological parameters calculated by the computer 206.

In the example shown in FIG. 2A, the camera 201, computer 206, and memory 205 together comprise a photoplethysmograph. Alternatively, in FIG. 2A, the camera 201, computer 206, memory 205, wireless communication modules 290, 292, and I/O device 207 together comprise a photoplethysmograph. Alternatively, in FIG. 2A, the camera 201, computer 206, memory 205, wireless communication modules 290, 292, I/O device 207, and light source module 240 together comprise a photoplethysmograph.

In some implementations of this invention, a contact PPG device touches the human's skin while the contact PPG device takes PPG measurements.

Figure 2B:
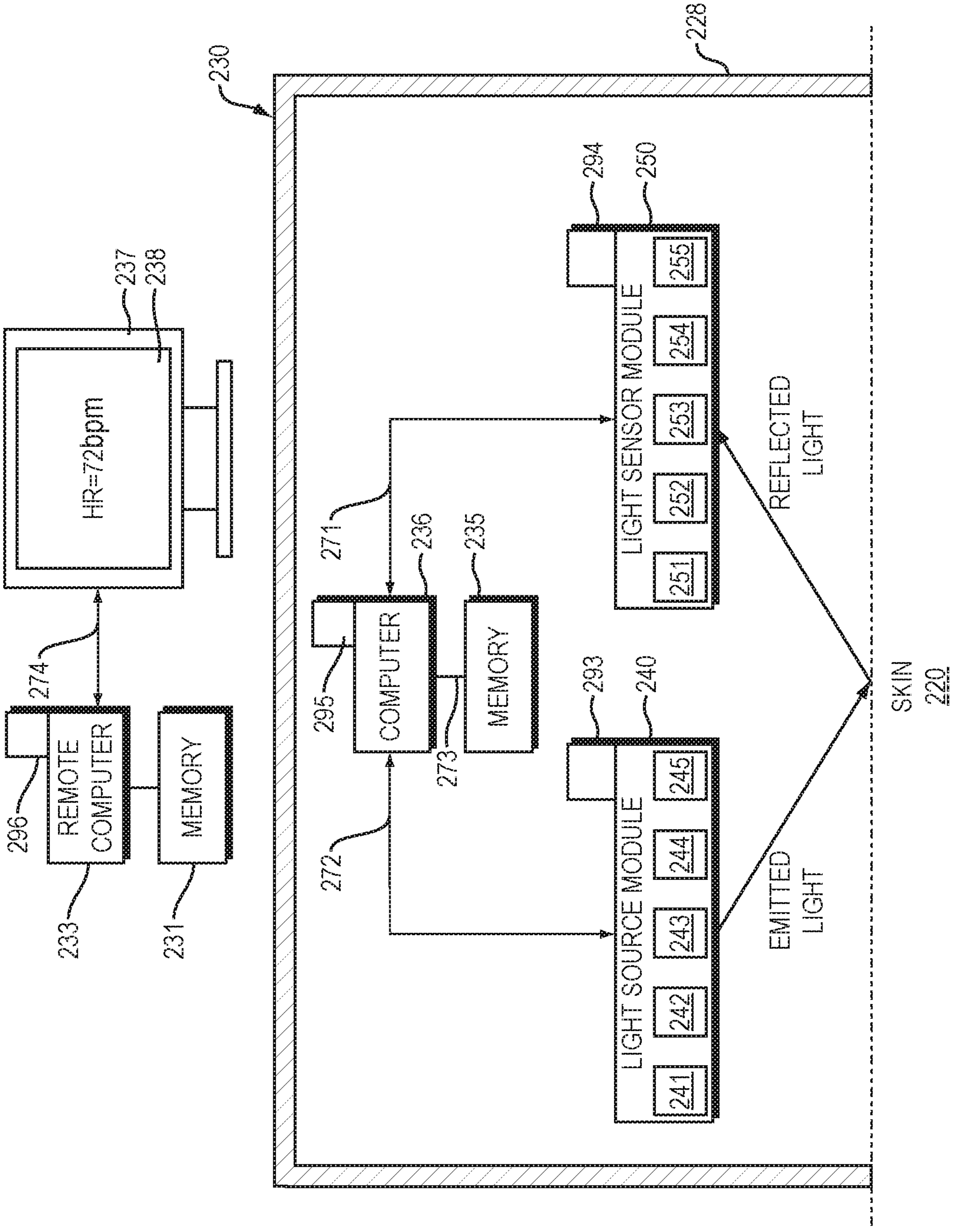
FIG. 2B shows hardware for contact PPG measurements.

FIG. 2B shows hardware for contact PPG measurements, in an illustrative implementation of this invention. In FIG. 2B, a contact PPG device 230 houses a light sensor module 250 and a light source module 240. A housing 228 of the contact PPG device 230 is in contact with a human's skin, while the contact PPG device 230 takes PPG measurements of the human.

The contact PPG device 230 includes a light source module 240, which comprises one or more active light sources, such as LEDs (light-emitting diodes).

In illustrative implementations, the light source module 240 includes any combination of three or more active light sources (e.g., LEDs), which combination includes at least one orange light source, one green light source, and one cyan light source. For example, in some cases, the light source module 240 includes at least one red light source 241, at least one orange light source 242, at least one green light source 243, at least one cyan light source 244, and at least one blue light source 245.

Alternatively, in some cases, the active light source module 240 includes only one or more orange light sources but does not include other light sources. Alternatively, in some cases, the light source module 240 includes any combination of two or more active light sources such that: (a) the light sources do not all emit the same spectral power distribution of light, and (b) at least one of the light sources is an orange light source. For example, in some cases, the light source module 240 comprises: (a) one or more orange light sources and one or more red light sources; (b) one or more orange light sources and one or more green light sources; and (c) one or more orange light sources, one or more red light sources, and one or more green light sources.

In the above examples, the light sources emit light in the visible light range. However, this invention is not limited to the visible light range. For example, in some cases, the light sources include one or more infrared light sources. In each of the above examples, the combination of light sources may include one or more infrared light sources, in addition to the visible light sources.

In the contact example shown in FIG. 2B, the contact PPG device 230 includes a light sensor module 250.

In illustrative implementations, light sensor module 250 comprises multiple light sensors 250, which measure light that is transmitted or reflected by the skin 220. In some cases, the light sensor module 250 includes any combination of three or more light sensors, which combination includes at least one orange light sensor, one green light sensor, and one cyan light sensor. For example, in some cases, the light sensor module 250 includes at least one red light sensor 251, at least one orange light sensor 252, at least one green light sensor 253, at least one cyan light sensor 254, and at least one blue light sensor 255.

Alternatively, in some cases, the light sensor module includes a single light sensor (e.g. 251) and does not include other light sensors. For example, in some cases, the light sensor module 250 includes only one or more orange light sensors but does not include other light sensors. Alternatively, in some cases, the light sensor module 250 includes any combination of two or more light sensors such that: (a) the light sensors do not all have the same spectral sensitivity profile, and (b) at least one of the light sensors is an orange light sensor. For example, in some cases, the light sensors comprise: (a) one or more orange light sensors and one or more red light sensors; (b) one or more orange light sensors and one or more green light sensors; and (c) one or more orange light sensors, one or more red light sensors, and one or more green light sensors.

In many implementations, for each given color of light source in the light source module 240, there is at least one light sensor of that given color in the light sensor module 250.

For example, in some cases, there are three colors of light sources and three corresponding colors of light sensors. For example, in some cases: (a) the light source module 240 includes at least one orange light source 242, at least one green light source 243, and at least one cyan light source 244; and (b) the light sensor module 250 includes at least one orange light sensor 252, at least one green light sensor 253, and at least one cyan light sensor 254.

For example, in some cases, there are five colors of light sources and five corresponding colors of light sensors. For example, in some cases: (a) the light source module 240 includes at least one red light source 241, at least one orange light source 242, at least one green light source 243, at least one cyan light source 244, and at least one blue light source 245; and (b) the light sensor module 250 includes at least one red light sensor 251, at least one orange light sensor 252, at least one green light sensor 253, at least one cyan light sensor 254, and at least one blue light sensor 255.

In many implementations, all of the light sources are on at the same time. For example, in many implementations (in which there are multiple colors of light sources and corresponding colors of light sensors), all of the light sources are on at the same time.

Alternatively, in some cases, the light sources are time-multiplexed, such that lights of different colors are on at different times. In some cases with time-multiplexed light sources, the one or more light sensors are all broadband. In other cases with time-multiplexed light sources, the colors of the light sources and light sensors correspond, such that for each given color of light source, there is at least one light sensor of that given color.

In some cases which involve time-multiplexing, a computer 236 generates control signals to time-multiplex the light sources in the light source module 240, such that different colors (or different combinations of colors) of light sources are on at different times. For example, in some cases, a computer 236 generates control signals that cause the active light sources to emit a time-multiplexed sequence of different colors or different combinations of colors. For example, in some cases, the sequence is such that only one color of light source is on at a time. For example, in some cases, first, the red light source 241 is on and the other light sources 242, 243, 244, 245 are off, then the orange light source 242 is on and the other light sources 241, 243, 244, 245 are off, then the green light source 243 is on and the other light sources 241, 242, 244, 245 are off, then the cyan light source 244 is on and the other light sources 241, 242, 243, 245 are off, and then the blue light source 245 is on and the other light sources 241, 242, 243, 244 are off In other cases, the sequence is such that different combinations of colors are emitted at different times.

In the example shown in FIG. 2B, the light sensor module 250 exports data to a computer 236 onboard the contact PPG device 230. In some cases, the onboard computer 236 forwards the data (in some cases, after processing) to a remote computer 233. The remote computer 233 takes the data as input, and calculates IBIs and SD-PPTs, and determines physiological parameters of the human, including one or more of the following parameters: heart rate, breath rate, heart rate variability (HRV), a high-frequency component of the HRV, and a low-frequency component of the HRV. The remote computer 233 also controls an I/O device 237, such as computer monitor or other display screen. The computer 233 causes the I/O device 237 to display a graphical user interface (GUI) 238. This GUI 238 displays, in human readable format, the physiological parameters calculated by computer 233. Computers 233 and 236 store data in memory devices 231 and 235, respectively.

Alternatively, the onboard computer 236 itself calculates the physiological parameters.

In illustrative implementations, hardware components communicate with each other via wired communication links (e.g., 204, 271, 272, 273, 274) or wireless communication links, or a combination of both. In those cases in which wireless communication is employed, wireless communication is between or among wireless communication modules (e.g., 290, 291, 293, 294, 295, 296).

In many implementations a remote camera images the skin, only ambient light illuminates the skin, and no active light sources are used to illuminate the skin. However, in some cases in which remote camera images the skin, a light source module 240 illuminate the skin. The light source module 240 comprises one or more active light sources (e.g., LEDs). In some cases, the light source module 240 and the remote camera 201 are positioned at the same distance from the skin. Alternatively, in some cases, the light source module 240 and the remote camera 201 are positioned at different distances from the skin. In some cases in which a remote camera images the skin, the light sources in light source module 240 emit different colors, as described above.

In the example shown in FIG. 2B, contact PPG device 230 comprises a photoplethysmograph. Alternatively, in FIG. 2B, contact PPG device 230, computer 233, memory 231, wireless communication module 296, and I/O device 237 together comprise a photoplethysmograph.

Figure 3:
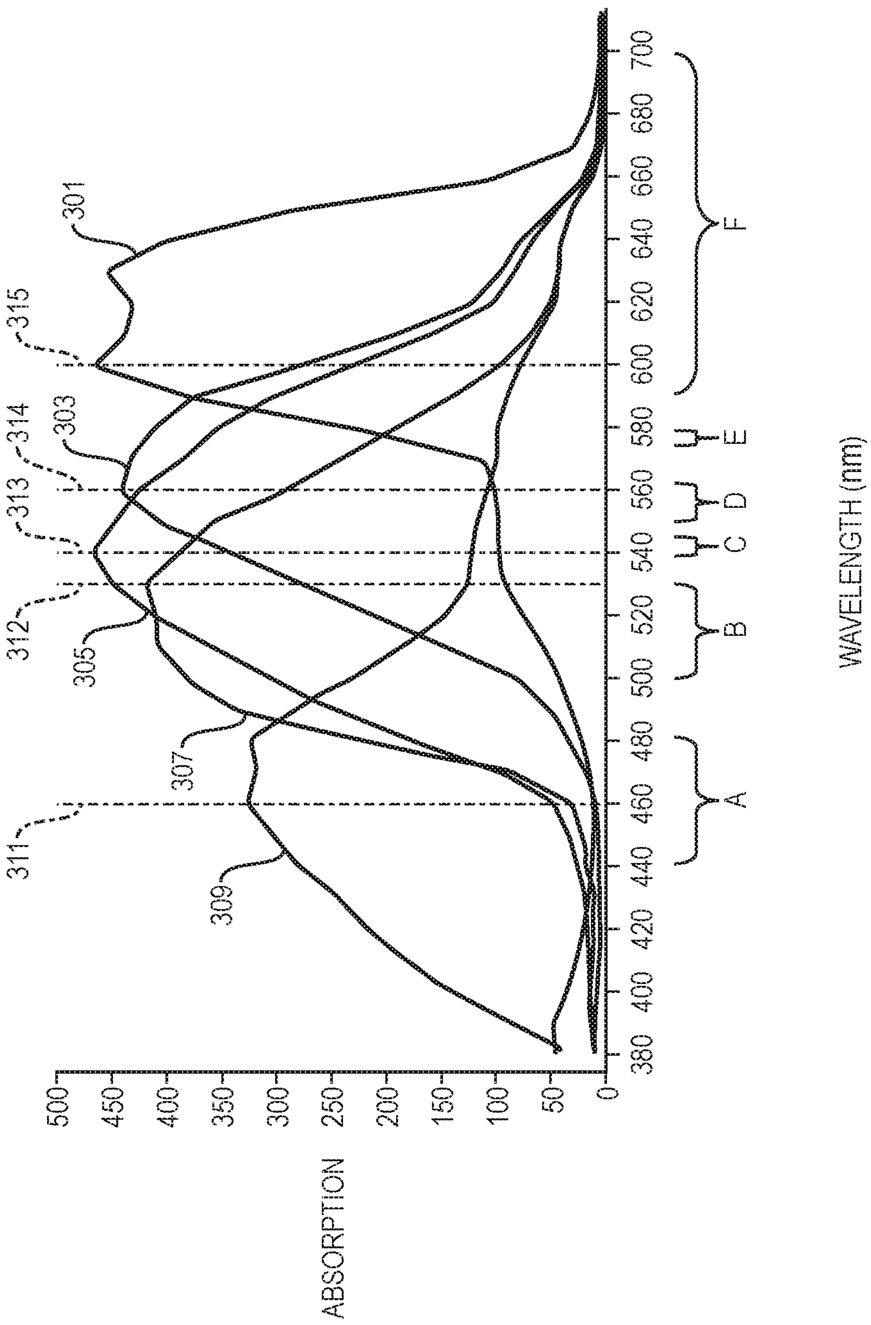
FIG. 3 is a chart showing an example of absorption spectra for five color bands (red, orange, green, cyan and blue) of a camera.

FIG. 3 is a chart showing an example of sensitivity profiles (also sometimes called absorption spectra) for five color channels of a camera. In this chart, the horizontal axis is the wavelength of light, and the vertical axis is a measure of absorption of light by camera pixels, which is in turn a measure of the pixels' sensitivity to light. The more sensitive that a pixel is to a particular wavelength of light, the more light that is absorbed by the pixel at that particular wavelength, and thus the higher the intensity of light recorded by the pixel at that particular wavelength. Likewise, the more sensitive that a color channel is to a particular wavelength of light, the more light that is absorbed by pixels in that color channel at that particular wavelength, and thus the higher the intensity of light recorded by pixels in that color channel at that particular wavelength. The raw intensity values captured by the camera for a given color channel are a function of, among other things, the sensitivity profile for that color channel. Specifically, in some cases, the raw intensity values for a given color channel are such that:

$$m = \sum_{\lambda} e(\lambda)s(\lambda)$$

where $e(\lambda)$ is the energy of light at a given wavelength $\lambda$ and $s(\lambda)$ is the camera sensitivity profile for the certain color channel.

In the example shown in FIG. 3: (a) the blue color channel 309 is most sensitive to light at 460 nm, and thus the highest sensitivity peak 311 of the blue color channel 309 is at 460 nm; (b) the cyan color channel 307 is most sensitive to light at 530 nm, and thus the highest sensitivity peak 312 of the cyan color channel is at 530 nm; (c) the green color channel 305 is most sensitive to light at 540 nm, and thus the highest sensitivity peak 313 of the green color channel is at 540 nm; (d) the orange color channel 303 is most sensitive to light at 560 nm, and thus the highest sensitivity peak 314 of the orange color channel 303 is at 560 nm; and (e) the red color channel 301 is most sensitive to light at 600 nm, and thus the highest sensitivity peak 315 of the red color channel is at 600 nm. These sensitivity peaks are absorption peaks, because the greater the sensitivity of a pixel is at a given wavelength, the greater is the amount of light absorbed by the pixel at the given wavelength.

Figure 4A:
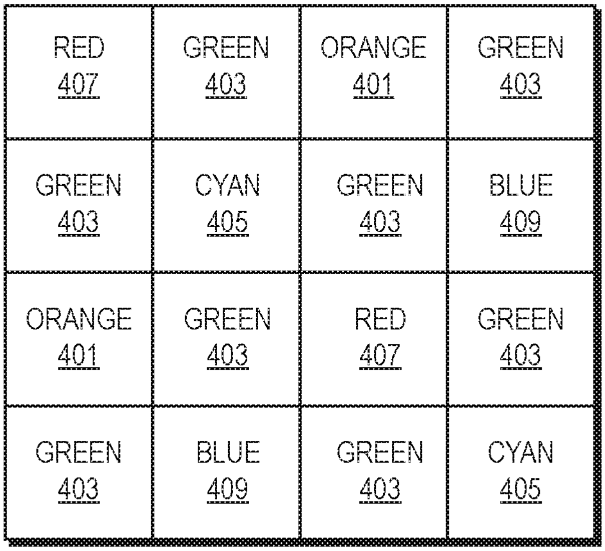
FIG. 4A shows a 4 pixel by 4 pixel pattern of pixels, with different color bands.

In illustrative implementations, the pixels of a CMOS camera are arranged in groups that are repeated across the CMOS sensor plane. Each group of pixels includes at least one pixel for each of the color bands. FIG. 4A shows a non-limiting example of a group of pixels. In FIG. 4A, a 4 pixel by 4 pixel group of pixels includes pixels from five different color bands: red pixels 407, orange pixels 401, green pixels 403, cyan pixels 405, and blue pixels 409. This arrangement of the colors in a 4×4 pattern repeats across the sensor plane. Each pixel on the sensor measures one color as determined by its position.

However, other patterns of pixels may be used, with different numbers of pixels per group, different shapes of the pixel group, or different combinations of colors of pixels in each group.

Figure 4B:
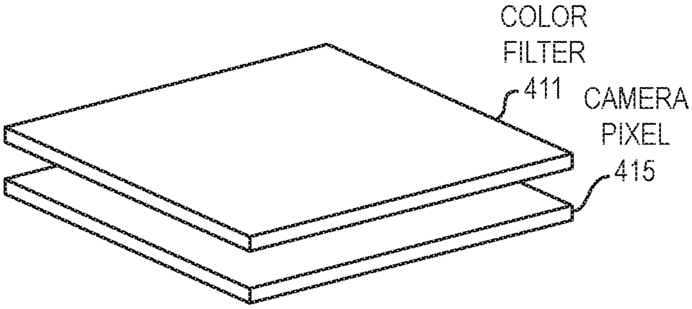
FIG. 4B shows a color filter over a pixel.

In some implementations, color filters are used to determine the color sensitivity of pixels. For example, in some cases, red, orange, green, cyan and blue filters are placed over pixels to make red, orange, green, cyan and blue pixels, respectively. FIG. 4B shows a color filter 411 over a camera pixel 415.

Figure 4C:
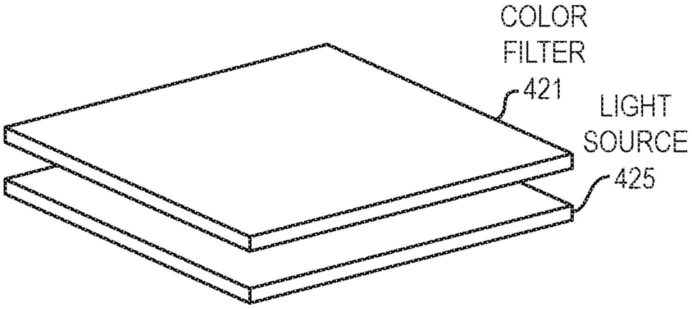
FIG. 4C shows a color filter over an active light source.

In some implementations, color filters are placed over active light sources. The color filters filter the light emitted by the light sources, and thereby determine the color of light emitted (after giving effect to the filtering). For example, in some cases, red, orange, green, cyan and blue filters are placed over active light sources (e.g., LEDs) to make red, orange, green, cyan and blue light sources, respectively. FIG. 4C shows a color filter 421 over an active light source 425.

Alternatively, in some cases, a filter is not used for one or more active light sources. In that case, the light source either emits a broad spectrum of light, or has an emission spectra (without a filter) that emits light in a desired frequency band.

In illustrative implementations, videos are recorded by a digital single lens reflex (DSLR) camera (e.g., at 30 fps, 960×720 resolution), and are exported in an uncompressed format. A computer analyzes the video recordings using software written in MATLAB®. This computer analysis is performed offline or in real time.

In illustrative implementations, a computer performs an algorithm ("Illustrative BVP Extraction Algorithm) to extract a BVP wave from the video. The Illustrative BVP Extraction Algorithm includes the following steps:

(1) Find the x- and y-coordinates of points on the face in each frame of the video. In some cases, this step is achieved by using a LEAR (Local Evidence Aggregation for Regression-based detection) algorithm for detecting facial points.

(2) Use the facial points to define a region of interest (ROI). In some cases, (a) the ROI comprises the full width between the outer eye corners (w) and a height twice the width (w above the eye corners to w below the eye corners) as a box encompassing the ROI, but (b) pixels are excluded from the ROI if the pixels are within a region around the eyes which is of width w and height w/2. (The pixels around the eyes are excluded in order to avoid motion artifacts due to eye blinking or eye movements). In some cases, the average ROI size is less than 25% of the frame.

(3) Calculate a spatial average of the color channel pixel values within the resulting ROI for each frame to form raw signals $x_1$ (t), $x_2$ (t), $x_N$(t), respectively (where N is the number of channels).

(4) Detrend the raw traces using a smoothness priors approach (e.g., with smoothness parameter λ set to 2000).

(5) Normalize the resulting signals by subtracting the mean and dividing by the standard deviation.

(6) Apply Independent Component Analysis (ICA) (e.g., a JADE implementation of ICA) to recover source signals from the observations, maximizing the non-Gaussianity within the sources.

(7) Band-pass filter each of the source signals using a Hamming window filter with low- and high-frequency cut-offs at 45 beats-per-minute (bpm) (0.75 Hz) and 270 bpm (4.5 Hz) respectively).

(8) Select the appropriate source signal, by calculating the normalized fast Fourier transform (FFT) of each source and choosing the source signal with the greatest frequency peak within the range 45-270 bpm.

(9) Scale the source by −1 if $\mu_{peakamp}<\mu_{troughamp}$.

Steps 4 to 7 of the Illustrative BVP Extraction Algorithm (above) are performed separately for each of color channels, respectively.

Step 8 of the Illustrative BVP Extraction Algorithm (above) is desirable because the ICA returns the source signals in arbitrary order, so that the same source signal does not always have the strongest BVP waveform). Step 8 corrects for this.

Step 9 of the Illustrative BVP Extraction Algorithm (above) is desirable the ICA may scale the source signals arbitrarily. If the scaling is by a negative number, the ICA flips the source signal, which is undesirable because the flip causes (if not corrected) less accurate readings. Step 9 corrects for this. For an inverted BVP signal, the mean trough amplitude is likely to be greater than the mean peak amplitude due to the shape of the BVP waveform. Therefore, to detect and correct for an inverted source signal (which has been inverted by ICA), a computer: (a) calculates the mean absolute peak amplitude $\mu_{peakamp}$ and mean absolute trough amplitude $\mu_{troughamp}$ of the source signal; and (b) inverts the source signal (that is, multiplies it by −1), if $\mu_{peakamp}<\mu_{troughamp}$.

In illustrative implementations, systolic peaks and diastolic inflection points (or peaks) are detected in an estimated BVP wave, as follows:

The systolic peaks (e.g., 101) occur at maxima within the BVP signal. In illustrative implementations, a computer determines systolic peak times from the BVP waveform, by performing an algorithm that includes the following steps. Interpolate the estimated BVP signal with a cubic spline function at a sampling frequency of 256 Hz. Locate the peaks in a moving time window of length 0.25 s. To avoid artifacts (such as motion or ectopic beats), filter peak intervals using the non-causal of variable threshold (NC-VT) algorithm (e.g., with a tolerance of 30%).

The diastolic inflections (e.g., 105) are more difficult to locate as they are not always maxima (and even if they are maxima, they are using much smaller than the systolic peaks). For most patients under most conditions, the largest (in magnitude) minimum within the second order derivative for a single heartbeat corresponds to the systolic peak and the next largest (in magnitude) minimum for that heartbeat corresponds to the diastolic inflection.

In illustrative implementations, a computer determines the time of diastolic peak (or inflection), by performing an algorithm that includes the following steps: Compute the second derivative of the BVP waveform. For example, if the algorithm is implemented in Matlab®, perform the MATLAB diff function twice on the signal. Then smooth the outputs with a three-point moving average filter. Invert the second derivative waveform. Perform peak detection on the inverted second derivative waveform. (For example, in some cases, peak detection is performed by treating a point as a peak if the point is a local maxima and has an intensity value that is greater than the preceding intensity value by at least 1% of the total signal amplitude). Identify the diastolic peak (or inflection) as the maximum following the systolic peak in each pulse cycle in the inverted second derivative pulse wave. Calculate the systolic-diastolic peak-to-peak times (SD-PPT) for each beat. Classify SD-PPT estimates that fall beyond one standard deviation from the mean as outliers and do not include these in the estimate of the final mean SD-PPT. (The reason for excluding these outliers is that the SD-PPTs are relatively stationary (compared to IBIs) within each two-minute session.

In illustrative implementations, each source signal returned by the ICA algorithm has a mean of zero. The peaks of the inverted second derivative of the BVP signal are troughs of the non-inverted second derivative of the BVP signal. Likewise, the troughs of the inverted second derivative of the BVP signal are peaks of the non-inverted second derivative of the BVP signal.

In illustrative implementations, a computer calculates an HRV spectrogram and the power of the high-frequency and low-frequency power components, respectively, of the HRV power spectra. To do so, a computer performs an algorithm ("Illustrative HRV Spectrogram Algorithm") that includes the following steps: Calculate the power spectral density (PSD) from the IBIs for sequential windows. For each window, calculate the power spectral density (PSD) of the inter-beat intervals using the Lomb periodogram. In this algorithm, use a moving window of one minute and step size of one second. Filter inter-beat intervals using a low pass filter with cut-off frequency 0.4 Hz. Calculate the high frequency (0.15-0.4 Hz) and low frequency (0.04-0.15 Hz) components of the HRV power spectra. As used herein: (a) the "high frequency component of the HRV power spectra" or "HF-HRV" means the high frequency (i.e., 0.15-0.4 Hz) component of the HRV power spectra; and (b) the "low frequency component of the HRV power spectra" or "LF-HRV" means the low frequency (i.e., 0.04-0.15 Hz) component of the HRV power spectra.

In illustrative implementations, a computer calculates breathing rate ("BR") from an HRV spectrogram. To do so, a computer performs an algorithm ("Illustrative BR Algorithm) that takes an estimated HRV spectrogram as an input and that calculates the breathing rate as the center frequency of the highest peak between 0.15 Hz and 0.4 Hz in the HRV power spectrum.

Figure 5:
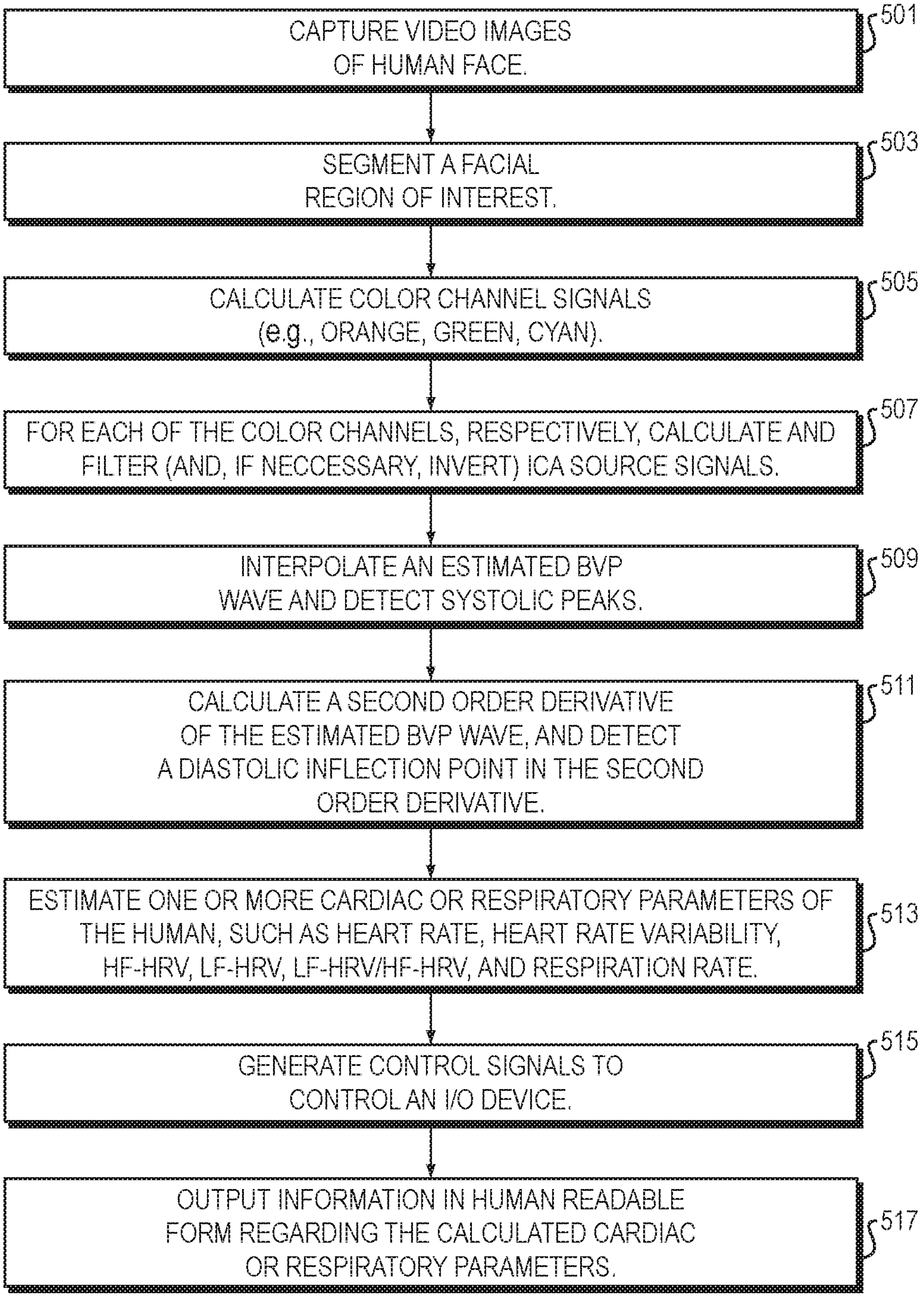
FIG. 5 shows steps in a method of calculating physiological parameters.

FIG. 5 shows steps in a method of calculating physiological parameters, in an illustrative implementation of this invention. The method in FIG. 5 includes at least the following steps. Capture video images of human face (Step 501). Segment a facial region of interest (Step 503). Calculate color channel signals (e.g., Orange, Green, Cyan) (Step 505). For each of the color channels, respectively, calculate and filter (and, if necessary, invert) ICA source signals (Step 507). Interpolate an estimated BVP wave and detect systolic peaks (Step 509). Calculate a second order derivative of the estimated BVP wave, and detect a diastolic inflection point in the second order derivative (Step 511). Estimate one or more cardiac or respiratory parameters of the human, such as heart rate, heart rate variability, HF-HRV (the high-frequency component of the HRV power spectra), LF-HRV (the low-frequency component of the HRV power spectra), LF-HRV/HF-HRV, and respiration rate (Step 513). Generate signals to control an I/O device (Step 515). Output information in human readable form regarding the calculated cardiac or respiratory parameters (Step 517). Steps 503, 505, 507, 509, 511 and 513 are performed by one or more computers.

Figure 6:
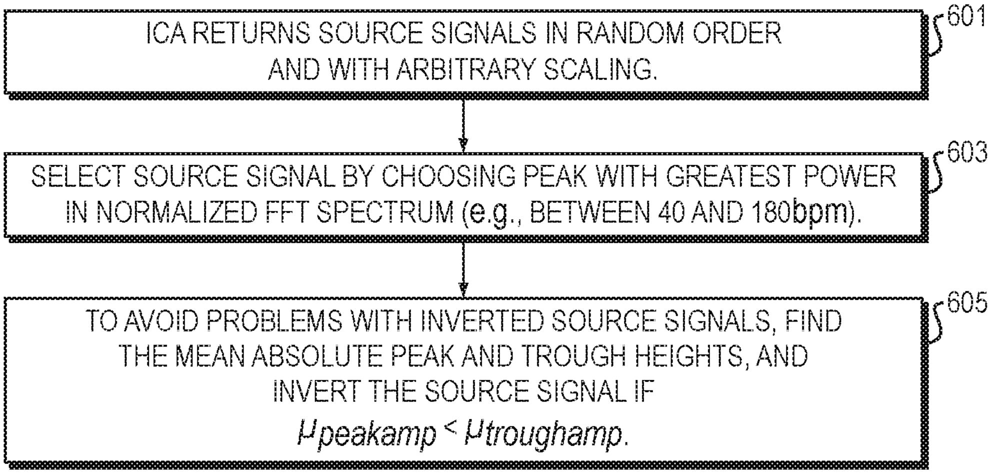
FIG. 6 shows steps in a method of inverting and scaling a source signal.

FIG. 6 shows steps in a method of inverting and scaling a source signal, in an illustrative implementation of this invention. ICA returns source signals in random order and with arbitrary scaling (Step 601). Select source signal by choosing peak with greatest power in normalized FFT spectrum (e.g., between 40 and 180 bpm) (Step 603). To avoid problems with inverted source signals, find the mean absolute peak and trough heights, and invert the source signal if $\mu_{peakamp}<\mu_{troughamp}$ (Step 605). Steps 601, 603, and 605 are performed by one or more computers.

In some cases, one or more tangible, non-transitory machine-readable media are employed. Each machine-readable medium stores instructions for a program for estimating a BVP wave, detecting IBIs and SD-PPTs, and determining heart rate. In some cases, the program also estimates one or more of the following: heart rate variability, HF-HRV (the high-frequency component of the HRV power spectra), LF-HRV (the low-frequency component of the HRV power spectra), spectral power ration LF-HRV/HF-HRV, and respiration rate. The program takes, as input, sensor data gathered by a contact PPG sensor (e.g., 230) or a remote PPG sensor (e.g., video camera 201).

Figure 7:
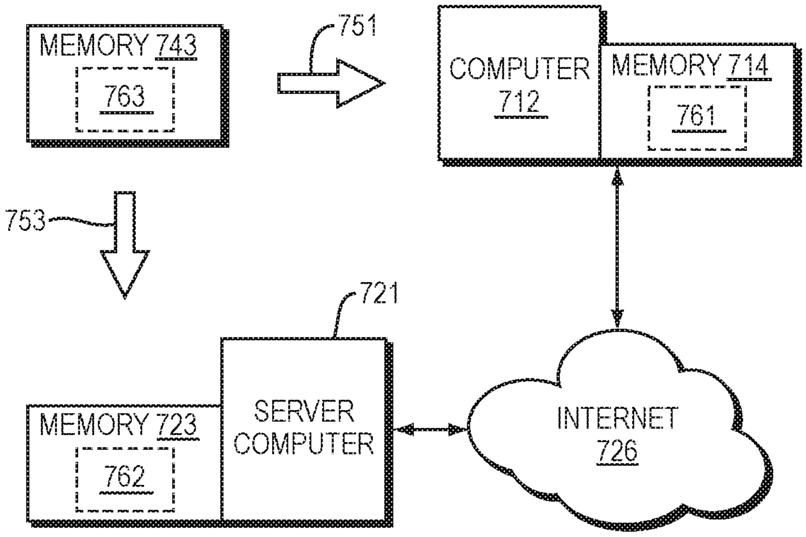
FIG. 7 shows examples of machine-readable media.

In the example shown in FIG. 7, three non-transitory machine-readable media 761, 762, 763 store identical copies of this program. Thus, each of the machine-readable media 761, 762, 763 stores the instructions for this program.

In FIG. 7, machine-readable medium 761 is part of memory device 714 for computer 712. Computer 712 (and machine-readable medium 761 and memory 714) are housed in a PPG sensor or are positioned external to the PPG sensor. Computer 712 executes the program, calculates heart rate and other physiological parameters, and outputs the calculated parameters for display on an I/O device.

In FIG. 7, machine-readable medium 762 is part of memory device 723, which is part of, or auxiliary to, server computer 721. Server computer 721 is connected to the Internet 726. In some cases, the program is downloaded from the server computer via the Internet 726. For example, in some cases, the download involves transferring a copy of the encoded program instructions from machine-readable medium 762 to server computer 721, then over the Internet 726 to computer 712, and then to machine-readable medium 761, which is part of memory device 714.

In FIG. 7, machine-readable medium 763 comprises all or part of a memory device 743. For example, in some cases, machine-readable medium 763 stores a master copy or backup copy of the encoded program instructions. In some cases, the program instructions encoded in the master copy are copied 751 into machine-readable medium 761 during manufacturing. In some cases, the program instructions encoded in the master copy are copied 753 into machine-readable medium 762, which is used in downloading the program, as discussed above.

In some cases, a non-transitory, machine-readable medium (e.g., 761, 762, or 763) comprises part or all of an electronic memory storage device, such as a RAM (random-access memory), DRAM (dynamic random-access memory), ROM (read only memory), PROM (programmable read only memory), EPROM (erasable programmable read only memory), or EEPROM (electrically erasable programmable read only memory) device; and (b) the program is encoded in voltage levels in a set of electronic components (e.g., flip-flops or latches) in the medium. In some cases: (a) voltage levels in hardware components of the machine-readable medium encode a set of logic states that do not change throughout an entire time interval that has a non-zero duration, and (b) the hardware components of the machine-readable medium exist throughout this entire time period. Alternatively, a machine-readable medium (e.g., 761, 762, or 763) comprises part or all of a CD-ROM or other optical disc storage device, and a computer reads data or instructions stored in the CD-ROM by using an optical disc driver.

Prototype

The following is a description of a prototype of this invention. This prototype is a non-limiting example of this invention. This invention may be implemented in many other ways.

In this prototype (the "Prototype"), the camera is a digital single-lens reflex (DSLR) camera with a Zuiko® 50 mm lens. The camera has a five color band CMOS sensor for capturing five color bands. The CMOS sensor includes red, orange, green, cyan and blue (ROGCB) frequency band pixels. Specifically, the camera's CMOS sensor has pixels for detecting light in the orange and cyan frequency bands as well as pixels for detecting light in the red, green and blue bands. The red, orange, green, cyan and blue pixels have the color sensitivities shown in FIG. 3.

In this prototype, videos are recorded at a frame rate of 30 frames per second (fps) and a resolution of 960×720. The video recording is in color (80-bit image with five channels× 16 bits/channel).

This invention is not limited to the above-described prototype. Instead, this invention can be implemented in many different ways.

Evaluation of Prototype, General

Two trials were performed to evaluate the Prototype. One trial ("Trial A") involved 14 participants; another trial ("Trial B") involved 10 participants. In the two trials, performance of the Prototype was compared to the performance of a conventional finger-worn contact PPG device.

The following test protocol was followed:

Trials A and B were conducted indoors with a varying amount of sunlight and indoor illumination. Participants were seated 3 meters from the camera and the data was recorded on a Toshiba® laptop running Windows® 7. During each trial, participants faced the camera while the videos were recorded. Two minute recordings of the participants were taken.

In each trial, the performance of the Prototype was compared to the performance of a conventional PPG contact sensor. Specifically, in each trial, physiological parameters extracted from PPG data gathered remotely by the camera of the Prototype were compared to physiological parameters extracted from PPG data gathered by the conventional contact PPG sensor. The conventional contact PPG sensor was an FDA-approved, Flexcomp® Infiniti contact PPG sensor, and was worn at the tip of the participant's left index finger during the trials. The conventional contact PPG sensor had a red LED for illuminating tissue (and no other colors of LEDs for illuminating tissue) and a red color channel sensor for measuring light reflected from the tissue (and no other sensor color channels for measuring the reflected light). In Trials A and B: (a) a conventional (Flexcomp® Infiniti) sensor measured respiration by detecting stretching of a band worn about the participant's chest; and (b) EDA (electro-dermal activity) sensors on the middle and ring fingers of each hand measured EDA.

In each trial, two recordings were taken for each participant, one at rest and one during a cognitive task. However, the cognitive task was performed after the measurements at rest. The measurements at rest were taken as follows: Participants were asked to sit still, look toward the camera and relax. The video and contact recordings were captured for two minutes. The measurements during a cognitive task were taken as follows: Participants were asked to perform a mental arithmetic test silently. Starting with the number 4000 they were required to subtract 7, then subtract 7 again, and so on, as quickly as possible. The video and contact recordings were captured for two minutes. The participants started the task immediately after the recordings were started. Nearly all the participants reported this task to be significantly more stressful than the rest period.

Trial A

In Trial A, a computer performed the Illustrative BVP Extraction Algorithm described above. Among other things, the computer calculated the second derivative of BVP waves, as discussed above.

In Trial A, the Prototype took remote measurements of 14 healthy participants of both genders (eight females), different ages (18-35) and skin color.

In Trial A, for three participants, the conventional contact sensor measurements were noisy and had a number of unverifiable systolic and diastolic peaks. The data from these three participants was excluded. In Trial A, excluding the data from the noisy contact measurements left 22 two minute sessions by 11 participants.

Table 1 below shows the mean percentage absolute error and the mean absolute error for systolic peak times, in Trial A. These errors are between systolic peak times (i) as measured by a conventional Flexcomp® Infiniti contact PPG sensor attached to the fingertip of the left index finger, and (ii) as measured remotely by the Prototype. Table 1 also shows the mean percentage absolute error and the mean absolute error for systolic-diastolic peak to peak times (SD-PPTs), in Trial A. These errors are between SD-PPTs (i) as measured by the conventional Flexcomp® Infiniti contact PPG sensor (the "contact" measurements) and (ii) as measured remotely by the Prototype (the "remote" measurements). The means in Table I were calculated from data for all 22 sessions in Trial A (11 resting sessions, one for each of the 11 non-excluded participants, and 11 cognitive stress sessions, one for each of the 11 non-excluded participants).

TABLE I

| | | Channels | | | |
|---|---|---|---|---|---|
| | | G | RGB | OGC | ROGCB |
| IBIs | % Ab. Error | 5.12* | 8.72 | 3.10** | 3.10** |
| | Ab. Error (s) | 0.045* | 0.076 | 0.026** | 0.026** |
| Mean SD-PPT | % Ab. Error | 5.47 | 5.79 | 4.11 | 4.13 |
| | Ab. Error (s) | 0.016 | 0.017 | 0.012 | 0.013 |

In Table I "*" means significantly lower error than RGB ($p<0.05$). In Table I, "*" means significantly lower error than both G and RGB ($p<0.05$)

Table I compares the results obtained by using just the green channel (G), the red, green and blue channels (RGB), the orange, green and cyan channels (OGC) and all channels (ROGCB). The absolute error between the contact and remotely measured IBIs using OGC is 0.026 s (this represents only 3% error). The errors between the contact and remotely measured mean SD-PPTs are also small, 0.012 s absolute error, using OGC channels (this represents 4% error in SD-PPT timing). The accurate estimation of systolic and diastolic peak locations is particularly good considering that the sampling rate of the video was only 30 Hz. The OGC channel combination significantly outperforms the green and RGB channels for measurement of physiological parameters (here the significances were computed using two-sample Kolmogorov-Smirnov tests). The OGC channels performs equivalently to the ROGCB combination. Again, this suggests there is no added benefit of the red and blue channels.

The results in Table I show that the best performance of the Prototype is obtained with a combination of green, orange and cyan color channels in the camera. As Table I shows, using a combination of the orange, green and cyan channels yields significantly better ($p<0.01$) results than using just the green signal or the traditional RGB combination.

Trial B

In Trial B, the Prototype took remote measurements of 10 participants of both genders (seven females), different ages (18-30) and multiple skin colors (Asian, Caucasian, Hispanic). Two participants were wearing glasses and one had facial hair.

In Trial B, in order to compute an estimated BVP wave from measurements taken by the Prototype, a computer performed the Illustrative BVP Extraction Algorithm, as described above, with the following modification: The high frequency cut-off for the Hamming filter was set at 180 bpm (3 Hz), instead of 270 bpm (4.5 Hz).

In Trial B, in order to compute the LF-HRV and HF-HRV from measurements taken by the Prototype, a computer performed the Illustrative HRV Spectrogram Algorithm, as described above.

In Trial B, in order to compute the breathing rate from measurements taken by the Prototype, a computer performed the Illustrative BR Algorithm, as described above. In Trial B, the breath-rate readings taken by Prototype were compared to breath-rate readings taken by the conventional sensor that measured stretching of a chest strap. For the conventional chest strap sensor, the breath rate was calculated as the frequency of the dominant peak in the PSD of the respiratory waveform.

In Trial B, experiments were performed with different combinations of color channels of the Prototype. Specifically, the performance of the Prototype using all possible combinations of the ROGBC (red, orange, green, cyan and blue) color bands was evaluated. Results are set forth in Table II below.

TABLE II

| | HR | BR | LF | HF | LF/HF | Lowest r |
|---|---|---|---|---|---|---|
| R | 0.99 | 0.95 | 0.60 | 0.60 | 0.57 | O |
| G | 0.99 | 0.91 | 0.63 | 0.63 | 0.63 | RGB |
| B | 0.99 | 0.93 | 0.68 | 0.68 | 0.70 | CO |
| C | 0.85 | 0.44 | 0.64 | 0.64 | 0.64 | GB |
| O | 0.83 | −0.02 | 0.43 | 0.43 | 0.34 | C |
| RG | 0.97 | 0.66 | 0.72 | 0.72 | 0.74 | RB |
| RB | 0.95 | 0.89 | 0.47 | 0.47 | 0.47 | BC |
| RC | 0.99 | 0.67 | 0.69 | 0.69 | 0.73 | R |
| RO | 1.00 | 0.93 | 0.88 | 0.88 | 0.89 | RC |
| GB | 0.89 | 0.75 | 0.44 | 0.44 | 0.44 | RBC |
| GC | 0.99 | 0.83 | 0.82 | 0.82 | 0.82 | G |
| GO | 1.00 | 0.98 | 0.88 | 0.88 | 0.88 | RGC |
| BC | 0.99 | 0.68 | 0.61 | 0.61 | 0.65 | RG |
| BO | 1.00 | 0.92 | 0.87 | 0.87 | 0.87 | BCO |

TABLE II-continued

| | HR | BR | LF | HF | LF/HF | Lowest r |
|---|---|---|---|---|---|---|
| CO | 0.99 | 0.67 | 0.40 | 0.40 | 0.48 | B |
| RGB | 0.85 | 0.67 | 0.45 | 0.45 | 0.46 | RGBC |
| RGC | 0.99 | 0.75 | 0.67 | 0.67 | 0.71 | GBC |
| RGO | 1.00 | 0.92 | 0.83 | 0.83 | 0.86 | RGBCO |
| RBC | 0.99 | 0.69 | 0.71 | 0.71 | 0.68 | GBCO |
| RBO | 1.00 | 0.92 | 0.83 | 0.83 | 0.83 | RGBO |
| RCO | 1.00 | 0.90 | 0.91 | 0.91 | 0.89 | GC |
| GBC | 0.99 | 0.77 | 0.80 | 0.80 | 0.78 | RBCO |
| GBO | 1.00 | 0.93 | 0.84 | 0.84 | 0.83 | RBO |
| GCO | 1.00 | 0.93 | 0.93 | 0.93 | 0.93 | GBO |
| BCO | 0.99 | 0.84 | 0.69 | 0.69 | 0.77 | RGO |
| RGBC | 0.99 | 0.89 | 0.72 | 0.72 | 0.68 | RGCO |
| RGBO | 1.00 | 0.81 | 0.79 | 0.79 | 0.81 | BO |
| RGCO | 1.00 | 0.90 | 0.87 | 0.87 | 0.86 | RO |
| RBCO | 1.00 | 0.90 | 0.81 | 0.81 | 0.77 | RCO |
| GBCO | 1.00 | 0.72 | 0.83 | 0.83 | 0.80 | GO |
| RGBCO | 1.00 | 0.74 | 0.81 | 0.81 | 0.79 | GCO |
| | | | | | | Highest r |

Table II is a comparison of the correlations between the conventional contact sensor measurements and the remote PPG measurements taken by the Prototype, for all combinations of R (red), G (green), B (blue), C (cyan) and orange (O) color bands of a 5 color band digital camera. For all of these correlations, <0.01.

The right column of Table II orders the color channel combinations from lowest mean correlation $\bar{r}$ to highest mean correlation $\bar{r}$. Specifically, the right column of Table II shows the color channel combinations ordered with respect to ascending mean HR, BR, LF, HF and LF/HF correlation $\bar{r}$. The mean correlation $\bar{r}$ for a given color channel is the mean of the correlations (between the conventional contact sensor measurements and the remote Prototype measurements) for the given color channel for HR (heart rate), BR (breath rate), LF (that is, LF-HRV), HF (that is, HF-HRV) and LF/HF. For example, Table II indicates that the mean correlation r for the RGBCO color channel is the mean of 1.00, 0.74, 0.81, 0.81 and 0.79.

As shown by right column of Table II, the GCO (green, cyan, orange) combination of color channels performed best, that is, had the highest mean correlation $\bar{r}$.

As shown by the right column of Table II, an orange color channel was present in each of the ten best performing combinations of color channels (that is, the ten combinations of color channels with the highest mean correlations $\bar{r}$). Yet, counter-intuitively, the orange color channel by itself performed worst, that is, had the lowest mean correlation $\bar{r}$.

Interestingly, the RGB combination of color channels, used in today's standard digital cameras, was one of the worst performing combinations of channels.

In this prototype, the maximum sensitivity of the green color channel coincides with in an absorption peak for oxy-hemoglobin. Likewise, in this prototype, the maximum sensitivity of the orange color channel coincides with an absorption peak for hemoglobin.

Consider the ranges of wavelengths that are labeled A, B, C, D, E, and F, respectively, in FIG. 3. Range A is all wavelengths between 440 nm and 485 nm. Range B is all wavelengths between 505 nm and 533 nm. Range C is all wavelengths between 538 nm and 544 nm. Range D is all wavelengths between 548 nm and 562 nm. Range E is all wavelengths between 574 nm and 578 nm. Range F is all wavelengths between 590 nm and 700 nm.

In the example shown in FIG. 3, the blue, cyan, green, orange and red color channels have sensitivity profiles 309, 307, 305, 303 and 301, respectively. In FIG. 3, the blue, cyan, green, orange and red color channels have their highest sensitivity at 311, 312, 313, 314, 315, respectively. These sensitivity peaks 311, 312, 313, 314, 315 occur in ranges A, B, C, D and F, respectively.

Two of these ranges correspond to an absorption peak for oxy-hemoglobin (HbO2) and an absorption peak for hemoglobin (Hb), respectively. Specifically, an absorption peak for oxy-hemoglobin occurs at Range C (i.e., 538 nm-544 nm) and an absorption peak for hemoglobin (Hb) occurs at Range D (i.e., 548 nm-562 nm). Thus, both an absorption peak of oxy-hemoglobin and the maximum sensitivity of the green color channel occur in the range of 538 nm-544 nm (that is, Range C). Likewise, both an absorption peak of hemoglobin and the maximum sensitivity of the orange color channel occur in the range of 548 nm-562 nm (that is, Range D)

During a peripheral pulse wave, the volume of blood at or near the skin changes, and thus the volumes of oxy-hemoglobin and hemoglobin at or near the skin changes. The green color channel and orange color channels are extremely sensitive to reflected light from oxy-hemoglobin and hemoglobin, respectively. Without being limited by theory, it appears that this is because the sensitivity peaks of the green and orange color channels correspond to absorption peaks of oxy-hemoglobin and hemoglobin, respectively, as discussed above.

Range E in FIG. 3 (i.e., 574 nm-578 nm) is another absorption peak of oxy-hemoglobin.

The maximum sensitivity of the cyan channel does not coincide with an absorption peak for hemoglobin or oxy-hemoglobin. Yet the experimental results (discussed above) show that a combination of orange, green and cyan color channels is the most accurate. Without being limited by theory, it appears that including the cyan color channel is beneficial because including a noisy channel may make it easier for an Independent Component Analysis to disambiguate the signal and noise, by identifying them as different sources.

One of the advantages of measuring signals from multiple color channels and then applying Independent Component Analysis (ICA) is that if one color channel picks up a strong signal plus some noise and another color channel picks up mostly noise and some signal then the ICA is able to disambiguate the signal and noise (by identifying them as different sources) very well. Without being limited by theory, it appears that, in the example shown in FIG. 3, the fact that the cyan color channel's maximum sensitivity does not correspond to an absorption peak of hemoglobin or oxy-hemoglobin is beneficial, because the cyan band therefore picks up noise that is impacting the orange and green channels."

Computers

In exemplary implementations of this invention, one or more electronic computers (e.g. 206, 233, 236, 712) are programmed and specially adapted: (1) to control the operation of, or interface with, hardware components of a PPG sensor, including a camera or other light sensors, light sources, and wireless communication modules; (2) to take PPG sensor data as input and to estimate a BVP wave, measure IBIs and SD-PPTs, and calculate one or more physiological parameters (e.g., one or more of heart rate, heart rate variability, HF-HRV, LF-HRV, LF-HRV/HF-HRV, respiration rate, or arterial stiffness), and one or more other parameters indicated by the physiological parameters (e.g., stress or anxiety); (3) to perform any other calculation, computation, program, algorithm, computer function or computer task described or implied above; (4) to receive signals indicative of human input; (5) to output signals for controlling transducers for outputting information in human perceivable format; and (6) to process data, to perform computations, to execute any algorithm or software, and to control the read or write of data to and from memory devices. The one or more computers may be in any position or positions within or outside of the PPG sensor. For example, in some cases (a) at least one computer is housed in or together with other components of the PPG sensor, and (b) at least one computer is remote from other components of the PPG sensor. The one or more computers are connected to each other or to other devices either: (a) wirelessly, (b) by wired connection, or (c) by a combination of wired and wireless links.

In exemplary implementations, one or more computers are programmed to perform any and all calculations, computations, programs, algorithms, computer functions and computer tasks described or implied above. For example, in some cases: (a) a machine-accessible medium has instructions encoded thereon that specify steps in a software program; and (b) the computer accesses the instructions encoded on the machine-accessible medium, in order to determine steps to execute in the program. In exemplary implementations, the machine-accessible medium comprises a tangible non-transitory medium. In some cases, the machine-accessible medium comprises (a) a memory unit or (b) an auxiliary memory storage device. For example, in some cases, a control unit in a computer fetches the instructions from memory.

In illustrative implementations, one or more computers execute programs according to instructions encoded in one or more tangible, non-transitory, computer-readable media. For example, in some cases, these instructions comprise instructions for a computer to perform any calculation, computation, program, algorithm, computer function or computer task described or implied above. For example, in some cases, instructions encoded in a tangible, non-transitory, computer-accessible medium comprise instructions for a computer to: (1) to control the operation of, or interface with, hardware components of a PPG sensor, including a camera or other light sensors, active light sources, and wireless communication modules; (2) to take PPG sensor data as input and to estimate a BVP wave, measure IBIs and SD-PPTs, and calculate one or more physiological parameters (e.g., one or more of heart rate, heart rate variability, HF-HRV, LF-HRV, LF-HRV/HF-HRV, respiration rate, or arterial stiffness), and one or more other parameters indicated by the physiological parameters (e.g., stress or anxiety); (3) to perform any other calculation, computation, program, algorithm, computer function or computer task described or implied above; (4) to receive signals indicative of human input; (5) to output signals for controlling transducers for outputting information in human perceivable format; and (6) to process data, to perform computations, to execute any algorithm or software, and to control the read or write of data to and from memory devices.

Network Communication

In illustrative implementations of this invention, one or more computers or PPG sensors are configured for wireless or wired communication with other electronic devices in a network.

For example, in some cases, one or more computers or PPG sensors each include a wireless communication module for wireless communication with other electronic devices in a network. Each wireless communication module (e.g., 290, 291, 293, 294, 295, 296) includes (a) one or more antennas, (b) one or more wireless transceivers, transmitters or receivers, and (c) signal processing circuitry. The wireless communication module receives and transmits data in accordance with one or more wireless standards.

For example, in some cases, one or more of the following hardware components are used for network communication: a computer bus, a computer port, network connection, network interface device, host adapter, wireless module, wireless card, signal processor, modem, router, computer port, cables or wiring.

In some cases, one or more computers (e.g., onboard the same support structure as the sensor module) are programmed for communication over a network. For example, in some cases, one or more computers are programmed for network communication: (a) in accordance with the Internet Protocol Suite, or (b) in accordance with any other industry standard for communication, including any USB standard, ethernet standard (e.g., IEEE 802.3), token ring standard (e.g., IEEE 802.5), wireless standard (including IEEE 802.11 (wi-fi), IEEE 802.15 (bluetooth/zigbee), IEEE 802.16, IEEE 802.20 and including any mobile phone standard, including GSM (global system for mobile communications), UMTS (universal mobile telecommunication system), CDMA (code division multiple access, including IS-95, IS-2000, and WCDMA), or LTS (long term evolution)), or other IEEE communication standard.

In illustrative implementations of this invention, one or more computers or PPG sensors are configured for wireless or wired communication with other electronic devices in a network.

For example, in some cases, a PPG sensing system includes one or more of the following hardware components for network communication: a computer bus, a computer port, network connection, network interface device, host adapter, wireless module, wireless card, signal processor, modem, router, computer port, cables or wiring.

In some cases, one or more computers (e.g., including computers onboard or remote from a PPG sensor) are programmed for communication over a network. For example, in some cases, one or more computers are programmed for network communication: (a) in accordance with the Internet Protocol Suite, or (b) in accordance with any other industry standard for communication, including any USB standard, ethernet standard (e.g., IEEE 802.3), token ring standard (e.g., IEEE 802.5), wireless standard (including IEEE 802.11 (wi-fi), IEEE 802.15 (bluetooth/zigbee), IEEE 802.16, IEEE 802.20 and including any mobile phone standard, including GSM (global system for mobile communications), UMTS (universal mobile telecommunication system), CDMA (code division multiple access, including IS-95, IS-2000, and WCDMA), or LTS (long term evolution)), or other IEEE communication standard.

I/O Devices

In illustrative implementations, one or more computers or PPG sensor systems include, or interface with, I/O devices.

For example, in some cases, the I/O devices comprise one or more of the following: touch screens, cameras, microphones, speakers, accelerometers, gyroscopes, magnetometers, inertial measurement units, pressure sensors, touch sensors, capacitive sensors, buttons, dials, sliders, or transducers (e.g., haptic transducers).

In illustrative implementations, a human inputs data or instructions via one or more I/O devices. A computer outputs data or instructions (including data regarding physiological parameters) via one or more I/O devices.

Computer Program Listing

The attached Source Code takes multiple signals from different color band images and recovers the blood volume pulse (BVP) waveform. The number of color image bands may vary between 1 and N, where N is any integer. From the recovered BVP waveform the code is used to calculate the estimated heart rate (HR), respiration rate (RR) and heart rate variability (HRV) spectrum. As an intermediate step the code performs peak detection on the BVP waveform and computes the inter-beat intervals (IBIs).

Definitions

The terms "a" and "an", when modifying a noun, do not imply that only one of the noun exists.

To compute "based on" specified data means to perform a computation that takes the specified data as an input.

As used herein, x is "between" A and B if x is in the closed interval [A, B]. For example, a wavelength S is "between" 440 nm and 485 nm if $440 \leq S \leq 485$.

The term "bpm" means heartbeats per minute.

"BR" means breath rate.

"BVP" wave means a cardiac blood volume pulse wave.

Here are some non-limiting examples of a "camera": (a) a digital camera; (b) a video camera; (c) a light sensor or an array of light sensors; (d) an imaging system; (e) a light field camera or plenoptic camera; (g) a time-of-flight camera; or (h) an optical instrument that records images. A camera includes any computers or circuits that process data captured by the camera.

A blue "color channel" means a set of pixels that is most sensitive to a particular wavelength of light, which wavelength is between 440 nm and 485 nm. A cyan "color channel" means a set of pixels that is most sensitive to a particular wavelength of light, which wavelength is between 505 nm and 533 nm. A green "color channel" means a set of pixels that is most sensitive to a particular wavelength of light, which wavelength is between 538 nm and 544 nm. An orange "color channel" means a set of pixels that is most sensitive to a particular wavelength of light, which wavelength is between 548 nm and 562 nm. A red "color channel" means a set of pixels that is most sensitive to light in a range of wavelengths, which range is 590 nm to 700 nm. For example, in FIG. 3, pixels with sensitivity profiles 309, 307, 305, 303 and 301 are in the blue, cyan, green, orange and red color channels, respectively.

To say that a light sensor is a given color means that the light sensor is in a color channel of the given color. For example: (a) to say that a light sensor is "cyan" means that the light sensor is in a cyan color channel; (b) to say that a light sensor is "orange" means that the light sensor is in an orange color channel; (c) to say that a light sensor is "green" means that the light sensor is in a green color channel; (d) to say that a light sensor is "red" means that the light sensor is in a red color channel; and (e) to say that a light sensor is "blue" means that the light sensor is in a blue color channel.

A "blue" light source means a light source that emits light that is most intense at a particular wavelength of the light, which wavelength is between 440 nm and 485 nm. A "cyan" light source means a light source that emits light that is most intense at a particular wavelength of the light, which wavelength is between 505 nm and 533 nm. A "green" light source means a light source that emits light that is most intense at a particular wavelength of the light, which wavelength is between 538 nm and 544 nm. An "orange" light source means a light source that emits light that is most intense at a particular wavelength of the light, which wavelength is between 548 nm and 562 nm. A "red" light source means a set of pixels that is most sensitive to a particular wavelength of light, which wavelength is between 630 nm and 700 nm.

The term "comprise" (and grammatical variations thereof) shall be construed as if followed by "without limitation". If A comprises B, then A includes B and may include other things.

The term "computer" includes any computational device that performs logical and arithmetic operations. For example, in some cases, a "computer" comprises an electronic computational device, such as an integrated circuit, a microprocessor, a mobile computing device, a laptop computer, a tablet computer, a personal computer, or a mainframe computer. In some cases, a "computer" comprises: (a) a central processing unit, (b) an ALU (arithmetic logic unit), (c) a memory unit, and (d) a control unit that controls actions of other components of the computer so that encoded steps of a program are executed in a sequence. In some cases, a "computer" also includes peripheral units including an auxiliary memory storage device (e.g., a disk drive or flash memory), or includes signal processing circuitry. However, a human is not a "computer", as that term is used herein.

"Defined Term" means a term or phrase that is set forth in quotation marks in this Definitions section.

For an event to occur "during" a time period, it is not necessary that the event occur throughout the entire time period. For example, an event that occurs during only a portion of a given time period occurs "during" the given time period.

The term "e.g." means for example.

The fact that an "example" or multiple examples of something are given does not imply that they are the only instances of that thing. An example (or a group of examples) is merely a non-exhaustive and non-limiting illustration.

Unless the context clearly indicates otherwise: (1) a phrase that includes "a first" thing and "a second" thing does not imply an order of the two things (or that there are only two of the things); and (2) such a phrase is simply a way of identifying the two things, respectively, so that they each can be referred to later with specificity (e.g., by referring to "the first" thing and "the second" thing later). For example, unless the context clearly indicates otherwise, if an equation has a first term and a second term, then the equation may (or may not) have more than two terms, and the first term may occur before or after the second term in the equation. A phrase that includes a "third" thing, a "fourth" thing and so on shall be construed in like manner.

The term "for instance" means for example.

"Herein" means in this document, including text, specification, claims, abstract, and drawings.

"HF-HRV" means a high frequency (that is, 0.15-0.4 Hz) component of an HRV power spectrum.

"HR" means heart rate.

"HRV" means heart rate variability.

As used herein: (1) "implementation" means an implementation of this invention; (2) "embodiment" means an embodiment of this invention; (3) "case" means an implementation of this invention; and (4) "use scenario" means a use scenario of this invention.

The term "include" (and grammatical variations thereof) shall be construed as if followed by "without limitation".

"Intensity" means any measure of or related to intensity, energy or power. For example, the "intensity" of light includes any of the following measures: irradiance, spectral irradiance, radiant energy, radiant flux, spectral power, radiant intensity, spectral intensity, radiance, spectral radiance, radiant exitance, radiant emittance, spectral radiant exitance, spectral radiant emittance, radiosity, radiant exposure or radiant energy density.

"I/O device" means an input/output device. For example, an I/O device includes any device for (a) receiving input from a human, (b) providing output to a human, or (c) both. For example, an I/O device includes a user interface, graphical user interface, keyboard, mouse, touch screen, microphone, handheld controller, display screen, speaker, or projector for projecting a visual display. Also, for example, an I/O device includes any device (e.g., button, dial, knob, slider or haptic transducer) for receiving input from, or providing output to, a human.

"LF-HRV" means a low frequency (that is, 0.04-0.15 Hz) component of an HRV power spectrum.

"Light" means electromagnetic radiation of any frequency. For example, "light" includes, among other things, visible light and infrared light. Likewise, any term that directly or indirectly relates to light (e.g., "imaging") shall be construed broadly as applying to electromagnetic radiation of any frequency.

To "multiply" includes to multiply by an inverse. Thus, to "multiply" includes to divide.

The term "or" is inclusive, not exclusive. For example A or B is true if A is true, or B is true, or both A or B are true. Also, for example, a calculation of A or B means a calculation of A, or a calculation of B, or a calculation of A and B.

A parenthesis is simply to make text easier to read, by indicating a grouping of words. A parenthesis does not mean that the parenthetical material is optional or can be ignored.

"Photoplethysmograph" means a device that optically measures volume of a bodily fluid or tissue.

"PPG" means photoplethysmographic.

As used herein, the term "set" does not include a group with no elements. Mentioning a first set and a second set does not, in and of itself, create any implication regarding whether or not the first and second sets overlap (that is, intersect).

"Some" means one or more.

As used herein, a "subset" of a set consists of less than all of the elements of the set.

"Substantially" means at least ten percent. For example: (a) 112 is substantially larger than 100; and (b) 108 is not substantially larger than 100.

The term "such as" means for example.

To say that a machine-readable medium is "transitory" means that the medium is a transitory signal, such as an electromagnetic wave.

Except to the extent that the context clearly requires otherwise, if steps in a method are described herein, then the method includes variations in which: (1) steps in the method occur in any order or sequence, including any order or sequence different than that described; (2) any step or steps in the method occurs more than once; (3) different steps, out of the steps in the method, occur a different number of times during the method, (4) any combination of steps in the method is done in parallel or serially; (5) any step or steps in the method is performed iteratively; (6) a given step in the method is applied to the same thing each time that the given step occurs or is applied to different things each time that the given step occurs; or (7) the method includes other steps, in addition to the steps described.

This Definitions section shall, in all cases, control over and override any other definition of the Defined Terms. For example, the definitions of Defined Terms set forth in this Definitions section override common usage or any external dictionary. If a given term is explicitly or implicitly defined in this document, then that definition shall be controlling, and shall override any definition of the given term arising from any source (e.g., a dictionary or common usage) that is external to this document. If this document provides clarification regarding the meaning of a particular term, then that clarification shall, to the extent applicable, override any definition of the given term arising from any source (e.g., a dictionary or common usage) that is external to this document. To the extent that any term or phrase is defined or clarified herein, such definition or clarification applies to any grammatical variation of such term or phrase, taking into account the difference in grammatical form. For example, the grammatical variations include noun, verb, participle, adjective, and possessive forms, and different declensions, and different tenses. In each case described in this paragraph, Applicant is acting as Applicant's own lexicographer.

Variations:

This invention may be implemented in many different ways. Here are some non-limiting examples:

In one aspect, this invention is an apparatus comprising a photoplethysmograph, which photoplethysmograph includes at least three color channels, which color channels include an orange color channel, a green color channel and a cyan color channel. In some cases, the photoplethysmograph includes at least five color channels. In some cases, the photoplethysmograph includes at least an orange color channel, a green color channel, a cyan color channel, a red color channel and a blue color channel. In some cases, each of the color channels comprises a set of pixels in a video camera. In some cases, the photoplethysmograph is housed in a housing, which housing is configured to touch tissue while a camera in the photoplethysmograph captures light that reflects from, or is transmitted through, the tissue. In some cases, the photoplethysmograph includes at least three light sources, including an orange light source, a green light source, and a cyan light source. In some cases, the photoplethysmograph includes at least three light sources, including an orange light source, a green light source, and a cyan light source. Each of the cases described above in this paragraph is an example of the apparatus described in the first sentence of this paragraph, and is also an example of an embodiment of this invention that may be combined with other embodiments of this invention.

In another aspect, this invention is a method comprising, in combination: (a) a set of light sensors taking measurements of light that reflects from, or is transmitted through, tissue of a mammal; and (b) a computer taking, as input, data indicative of the measurements, and estimating a blood pulse volume wave; wherein the light sensors include at least three color channels, which color channels include an orange color channel, a green color channel and a cyan color channel. In some cases, the set of light sensors includes at least five color channels, which color channels include at least an orange color channel, a green color channel, a cyan color channel, a red color channel and a blue color channel. In some cases, the computer estimates a time interval between a systolic peak and a diastolic inflection, which peak and inflection occur during a single heartbeat of the blood pulse volume wave. In some cases, the computer calculates a second derivative of the blood pulse volume wave. In some cases, the light sensors comprise pixels in a digital video camera. In some cases, the camera is positioned more than a meter from the tissue while the measurements are taken. In some cases, the light sensors are housed in a housing, which housing does not touch the tissue while the measurements are taken. In some cases, the computer calculates at least a heart rate of the mammal. Each of the cases described above in this paragraph is an example of the method described in the first sentence of this paragraph, and is also an example of an embodiment of this invention that may be combined with other embodiments of this invention.

In another aspect, this invention is an apparatus comprising, in combination: (a) a set of light sensors for taking measurements of light that reflects from, or is transmitted through, tissue of a mammal; and (b) one or more computer that are programmed to take, as input, data indicative of the measurements, and to estimate a blood pulse volume wave; wherein the light sensors include at least three color channels, which color channels include an orange color channel, a green color channel and a cyan color channel. In some cases, the light sensors comprise pixels in a digital video camera. In some cases, the set of light sensors includes at least five color channels, which color channels include at least an orange color channel, a green color channel, a cyan color channel, a red color channel and a blue color channel. In some cases, the light sensors are housed in a housing, which housing is configured to touch tissue while the light sensors capture light that reflects from, or is transmitted through, the tissue. In some cases, the housing also houses at least three light sources, including an orange light source, a green light source, and a cyan light source. Each of the cases described above in this paragraph is an example of the apparatus described in the first sentence of this paragraph, and is also an example of an embodiment of this invention that may be combined with other embodiments of this invention.

In one aspect, this invention is an apparatus comprising, in combination: (a) a set of light sensors for taking measurements of light that reflects from, or is transmitted through, tissue of a mammal; (b) a computer; and (c) a non-transitory machine readable medium that has instructions encoded thereon for a computer to take, as input, data indicative of the measurements, and to estimate a blood pulse volume wave; wherein the light sensors include at least three color channels, which color channels include an orange color channel, a green color channel and a cyan color channel. In some cases, the light sensors include at least five color channels. In some cases, the light sensors include at least an orange color channel, a green color channel, a cyan color channel, a red color channel and a blue color channel. In some cases, the light sensors comprise pixels in a video camera. In some cases, the light sensors are in a housing, which housing is configured to touch tissue while the light sensors capture light that reflects from, or is transmitted through, the tissue. In some cases, the apparatus includes at least three light sources, including an orange light source, a green light source, and a cyan light source. In some cases, the instructions include instructions for the computer to estimate a time interval between a systolic peak and a diastolic inflection, which peak and inflection occur during a single heartbeat of the blood pulse volume wave. In some cases, the instructions include instructions for the computer to calculate a second derivative of the blood pulse volume wave. In some cases, the instructions include instructions for the computer to calculate at least a heart rate of the mammal. Each of the cases described above in this paragraph is an example of the apparatus described in the first sentence of this paragraph, and is also an example of an embodiment of this invention that may be combined with other embodiments of this invention.

The above description (including without limitation any attached drawings and figures) describes illustrative implementations of the invention. However, the invention may be implemented in other ways. The methods and apparatus which are described above are merely illustrative applications of the principles of the invention. Other arrangements, methods, modifications, and substitutions by one of ordinary skill in the art are therefore also within the scope of the present invention. Numerous modifications may be made by those skilled in the art without departing from the scope of the invention. Also, this invention includes without limitation each combination and permutation of one or more of the abovementioned implementations, embodiments and features.

What is claimed is:

1. Apparatus comprising a photoplethysmograph, which photoplethysmograph includes at least four color channels, which color channels include an orange color channel, a green color channel and a cyan color channel.

2. The apparatus of claim 1, wherein the four color channels further include a red color channel.

3. The apparatus of claim 1, wherein the four color channels further include a blue color channel.

4. The apparatus of claim 1, wherein each of the color channels comprises a set of pixels in a video camera.

5. The apparatus of claim 1, wherein the photoplethysmograph is housed in a housing, which housing is configured to touch tissue while a camera in the photoplethysmograph captures light that reflects from, or is transmitted through, the tissue.

6. The apparatus of claim 5, wherein the photoplethysmograph includes at least four light sources, including an orange light source, a green light source, and a cyan light source.

7. The apparatus of claim 1, wherein the photoplethysmograph includes at least four light sources, including an orange light source, a green light source, and a cyan light source.

* * * * *